United States Patent [19]

Safadago

[11] 4,354,485

[45] Oct. 19, 1982

[54] THERAPEUTIC APPARATUS FOR USE IN TREATMENT OF MUSCULAR AND SKELETAL DISORDERS

[76] Inventor: Gary J. Safadago, 5705 Seaview Ave. NW., Seattle, Wash. 98107

[21] Appl. No.: 130,592

[22] Filed: Mar. 17, 1980

Related U.S. Application Data

[62] Division of Ser. No. 711,469, Aug. 4, 1976, Pat. No. 4,207,879.

[51] Int. Cl.[3] .......... A61F 5/00

[52] U.S. Cl. .......... 128/70

[58] Field of Search .......... 128/69, 70, 78, 75; 269/328, 324

[56] References Cited

U.S. PATENT DOCUMENTS

| | | | |
|---|---|---|---|
| 2,492,920 | 12/1949 | Koster | 128/88 X |
| 3,320,949 | 5/1967 | Hatfield | 128/70 |
| 3,343,531 | 9/1967 | Thompson | 128/69 |
| 3,423,773 | 1/1969 | Yamate | 128/70 X |
| 3,434,165 | 3/1969 | Keane | 128/71 X |
| 3,675,646 | 7/1972 | Corcoran | 128/75 |

*Primary Examiner*—Michael H. Thaler
*Attorney, Agent, or Firm*—Robert W. Beach; Ward Brown; Douglas E. Winters

[57] ABSTRACT

A prone board is provided with an adjustable angle leg supporting and spreading appliance positioned to extend from a location below the crotch and between the thighs of a patient to a location below the patient's knees. The appliance is adjustable and cooperates with lateral foot supports for adaptation to progress in treatment of hip or knee extension and/or flexion. A face support relieves prolonged stress on the patient's neck or compensates for dysfunctional head support. An attachment including a leg inclined forwardly and a telescoping brace which permits adjustment of the angle of inclination of the prone board relative to the floor.

2 Claims, 13 Drawing Figures

Fig. 6
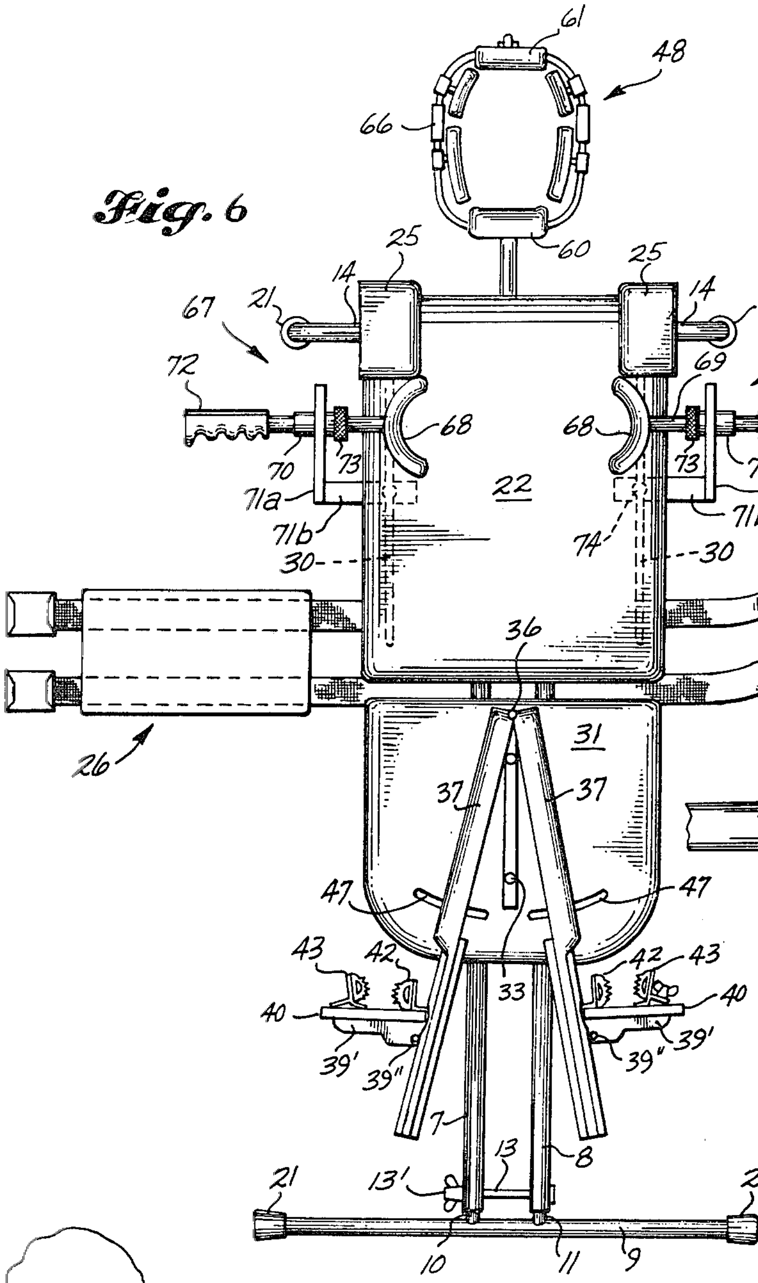
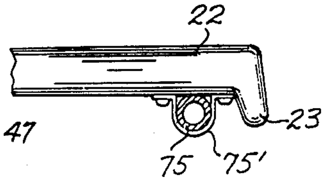
Fig. 13
Fig. 5
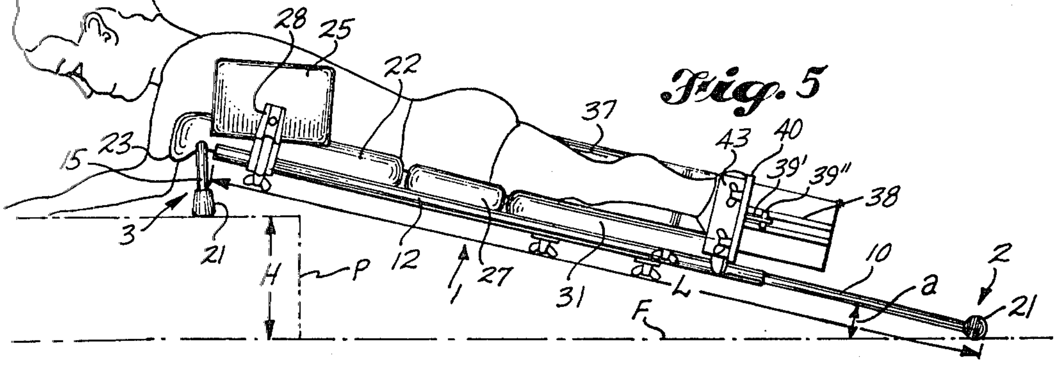

THERAPEUTIC APPARATUS FOR USE IN TREATMENT OF MUSCULAR AND SKELETAL DISORDERS

CROSS-REFERENCE

This application is a division of my copending application Ser. No. 711,469, filed Aug. 4, 1976, for Therapeutic Apparatus For Use In Treatment Of Muscular And Skeletal Disorders, now U.S. Pat. No. 4,207,879, issued June 17, 1980.

BACKGROUND OF THE INVENTION

1. Field of the Invention

The present invention relates to physical therapeutic apparatus commonly known as a prone board which is used in the treatment of children with disorders of the skeletal and muscular systems.

2. Prior Art

Prior prone boards have been provided which support the patient in a prone position and include a footrest. The end of the prone board remote from the footrest includes supporting legs which can be rested on platforms or tables of varied height to control the amount of the patient's weight supported by the legs and feet. Such prone boards have a frame consisting of a pair of lengthwise parallel tubes. One corresponding end of each tube is connected to a transverse linear support which normally rests on the floor. The opposite tube ends are connected to the laterally extending web of a U-shaped member, the legs of such member supporting the end of the frame on a platform of selected height from the floor. The frame carries a chest supporting board adjacent to the prone board end supported by the U-shaped member, which chest board extends from the upper sternum to the hips. Lateral supports prevent a patient from slipping sidewise from the chest supporting board. A hip belt is carried by the lower end of the chest supporting board to secure the patient thereto. A knee supporting board is mounted on the frame. For larger children where the space between the chest supporting and knee supporting boards is substantial and the hips are below the chest supporting board, an intermediate hip supporting board may be clamped to the frame. A footboard projects outward from the frame on which the soles of the patient's shoes rest. Brackets carried on the footrest anchor the feet in the spread and rotated positions selected by the therapist.

SUMMARY OF THE INVENTION

It is the principal object of the present invention to provide a prone board which is quickly, easily and accurately adjustable for adaptation to children of different sizes and having different degrees and combinations of skeletal and muscular disorders.

Another important object is to provide such adjustability for adaptation to changes in a particular patient due to growth and progress in treatment.

A further object is to provide appliances for a prone board which can be applied or detached quickly and easily to adapt the composite prone board to different combinations of disorders, different stages of growth and development of the child and different environmental conditions.

An additional object is to provide a prone board which can be used with a minimum of instruction by lay parents and guardians to permit therapeutic positions between professionally supervised therapeutic sessions.

A corollary object is to provide such a prone board which can be utilized to facilitate greater ranges of movement and play for the child and to reduce the restrictions on the child and its family relative to participation in a wide range of environments and activities.

Still another important object is to provide such versatility while assuring protection of the child from unintended movement of the prone board, dislocation of the child relative to the prone board or engagement with any hard or sharp objects. More specifically, it is an object to provide readily accessible adjusting mechanism which is located so that the child can neither manipulate such mechanism nor be injured by it.

More specific objects will be seen from the subsequent description of the present invention.

The foregoing objects can be accomplished by modifying the prior art prone board and providing appliances therefor. The floor engaging lateral member is connected telescopically to the lengthwise parallel supports forming the frame whereby the overall length of the prone board can be adjusted to accommodate children through a wider range of different heights and to permit the desired prone board inclination to be obtained relative to tables of standard height or other suitable furniture. The lateral pads of the trunk support are mounted thereon by adjustable brackets so that the pads can be moved inwardly or outwardly to positively engage the sides of the child's trunk and maintain a particular lateral position of the trunk when desired. Such adjustability also permits use for children, particularly infants, whose trunk control and stability may be relatively undeveloped so that a hip strap alone provides insufficient support.

The knee support of the present invention is elongated to support a substantial ventral portion of the thighs and carries a pair of lateral supports or interleg spacers engageable with leg portions between a location above and a location below the knees. Such lateral leg supports extend lengthwise of the prone board and are pivotably connected at their ends nearer the hips. Their opposite ends are swingable about the pivot connection to effect spreading of the knees and thighs, and the leg supports can be clamped in the desired spread position. A footrest is carried by an extension on the free end of each leg support and is adjustable lengthwise of the leg support. A pair of spaced lateral shoe clamping members are carried by the footrest and are relatively adjustable. Such leg supporting and foot supporting mechanism provides for more positive control of the legs and feet for treating different combinations and degrees of hip and knee extension and/or flexion and thigh and lower leg abduction.

The trunk supporting member may carry a pair of arcuate lateral support pads with the chords of the pad arcs extending lengthwise of the prone board. The arcuate pads are independently adjustable both lengthwise and laterally relative to the frame so that the pads can be relatively positioned to aid treatment of scoliosis.

A collar mounted between the parallel tubes near the upper end of the prone board receives one end portion of a rod which carries a face rest on its opposite end. The rod is removably clamped in the collar against relative movement. The face rest includes an oval segmented ring which carries a plurality of pads for supporting the chin, cheeks, temples and forehead. The ring is adjustable lengthwise of its major axis to vary the distance between the chin and forehead pads.

The prone board can be made freestanding and adjustable between a substantially horizontal position and a wide range of acute angles of inclination by a modified frame supporting appliance. Such appliance replaces the U-shaped frame upper end support which has short legs to be supported by a platform. A U-shaped support having legs longer than the maximum desired height of the prone board upper end is pivotably connected to the frame upper end. One end of a telescoping member is pivotably connected to the U-shaped member and the opposite end of the telescoping member is pivotably connected to the opposite end portion of the frame. The pivotable connections and telescoping member permit the U-shaped supporting member to be disposed in a position alongside the prone board frame for storage and in a selected one of a plurality of positions forming an obtuse angle with the frame to support the prone board at a therapeutically selected angle of inclination.

BRIEF DESCRIPTION OF THE DRAWINGS

FIG. 5 is a side elevation of the prone board in a representative therapeutic position showing a child supported thereby.

FIG. 6 is a top plan of a modified prone board including scoliosis-treating and face rest appliances.

FIG. 13 is a fragmentary side elevation of a portion of FIG. 10 with a part in section.

DETAILED DESCRIPTION

Figure 1:
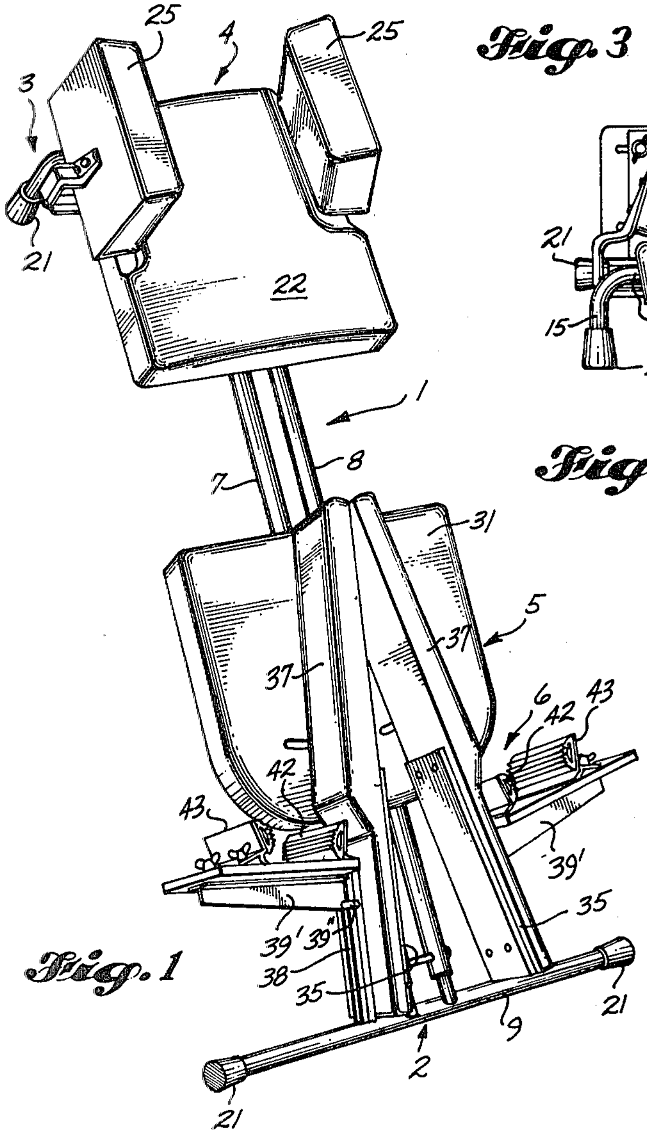
FIG. 1 is a top perspective of a prone board in accordance with the present invention.
Figure 2:
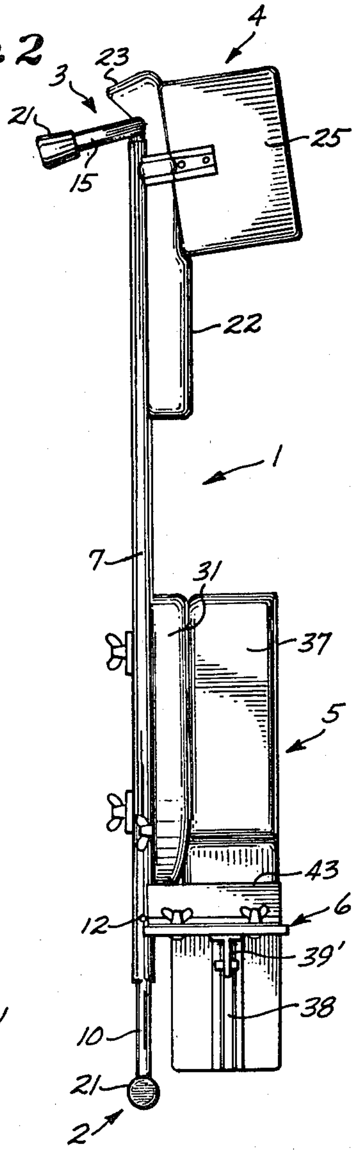
FIG. 2 is a side elevation of the prone board shown in FIG. 1.
Figure 3:
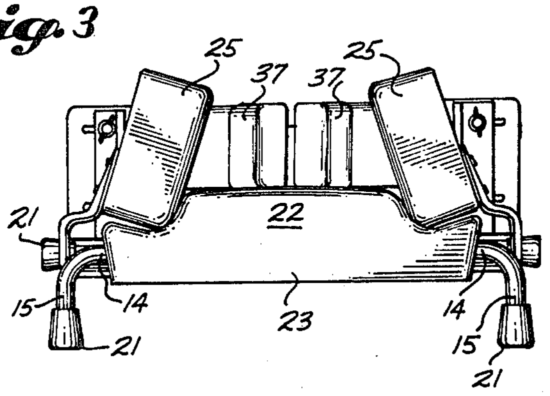
FIG. 3 is a head end elevation thereof and FIG. 4 is a foot end elevation thereof.
Figure 4:
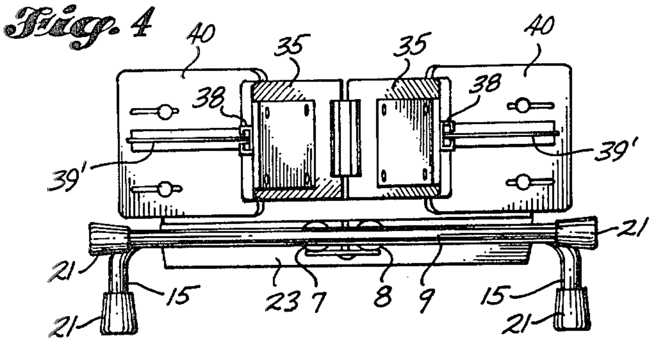

The prone board includes a frame 1, a frame foot end support 2, a frame head end support 3, patient trunk supporting structure 4, patient knee and leg supporting structure 5 and medial lateral leg and foot supporting mechanism 6. It is preferred that the frame and frame end supporting members be of tubular construction both to reduce the weight of the prone board and to facilitate mounting and demounting of prone board appliances as hereinafter described. It is further preferred that all portions which support and engage the body of a patient to be accommodated by the prone board be padded and upholstered. Variations in proportions and configurations of the body engaging members are shown among the drawing figures, many of such variations being a matter of choice, and only those variations of special significance will be described herein.

Figure 10:
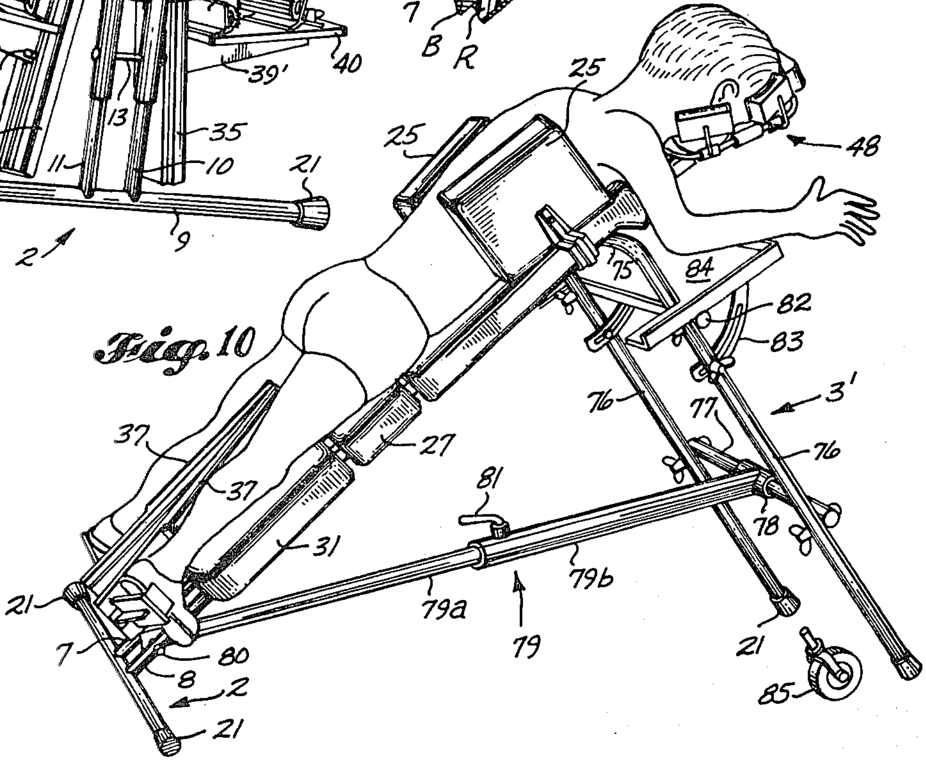
FIG. 10 is a top perspective of a prone board of the present invention including a self-supporting and inclination adjusting appliance.

Referring to FIGS. 1 through 8, the principal components of frame 1 are parallel tubular members 7 and 8 extending lengthwise of the prone board and of a patient supported thereon, which members define an axis of symmetry. The foot end of the frame is supported on a floor F by a linear support 9 extending transversely of frame members 7 and 8. In FIG. 10 member 9 is shown connected directly to the ends of frame members 7 and 8, but support member 9 may carry transverse rods or tubular members 10 and 11 shown in FIGS. 2, 5 and 6 having a row of aligned diametral bores therethrough. Frame members 7 and 8 have aligned diametral bores 12 (FIG. 2) adjacent to their lower ends. A set of bores in members 10,11 is aligned with the set of bores 12 in frame members 7,8, a bolt 13 (FIG. 6) is inserted through the aligned bores, and butterfly nut 13' is tightened to secure together the frame 1 and foot end support member 9.

As shown in FIg. 5, the distance L between the foot end support 2 and the head end support 3 determines the angle of inclination a with respect to a particular available platform P. This telescoping structure permits alteration of length L and, therefore, eliminates the necessity to provide a large number of custom height platforms in a therapeutic clinic. Furthermore, when the angle of inclination appropriate for a particular child is sufficiently large, standard height furniture of appropriate stability can be used in place of specific height platforms so that the prone board can be used at home or out of doors using the lower steps of stairs, picnic tables and the like as supporting platforms. Consequently, the therapeutic utility of the prone board can be extended in time, and a child can be moved about to participate in a greater variety of family activities with comfort and safety for the child and greater mobility for the child's guardians.

Figure 8:
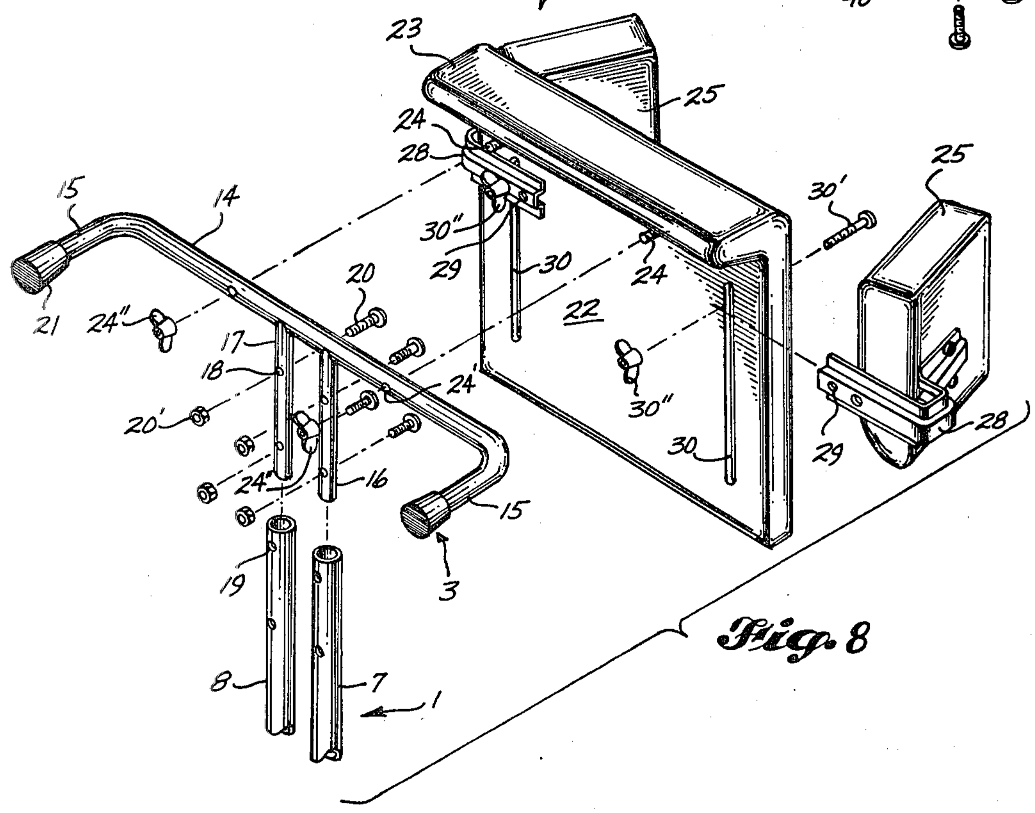
FIG. 8 is an exploded perspective of the trunk supporting member and the upper frame and frame end support, parts being broken away.

The frame head end support 3 includes a U-shaped member having a web 14 extending transversely of frame 1 and legs 15 projecting downwardly from the plane of the frame. While the web 14 could be welded or otherwise bonded to the ends of frame tubes 7 and 8, the preferred construction is shown in FIG. 8 whereby web 14 carries rods or tubes 16 and 17 telescopically inserted in frame tubes 7 and 8 respectively. Diametral bores 18 through rods 16 and 17 are aligned with diametral bores 19 through tubes 7 and 8 and bolts 20 and nuts 20' secure the frame and end support together. This construction not only facilitates assembly of the prone board but permits substitution of alternative supporting appliances. For example, U-shaped members having legs of different lengths may be used to increase the range of possible angles of inclination using a given supporting platform P.

Caps 21 of antiskid material such as natural or synthetic rubber are provided on the ends of floor engaging foot end support 2 and platform engaging head end support 3 to prevent movement of the prone board when a patient is placed on or removed from it or by movement of the patient while being supported on it.

Figure 11:
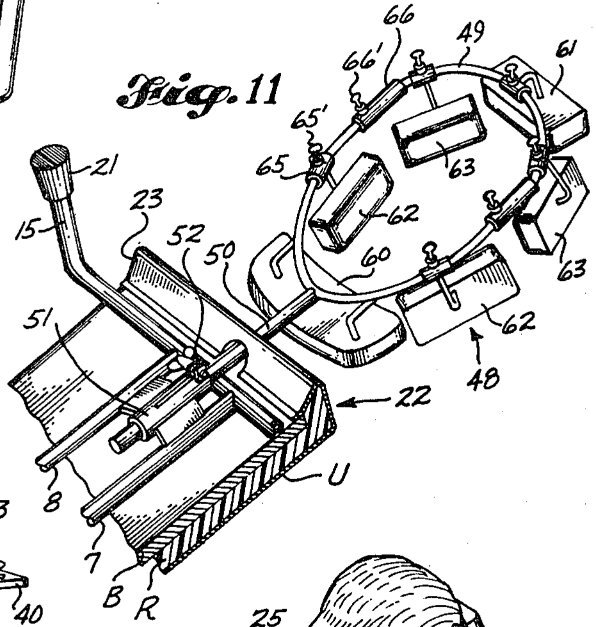
FIG. 11 is a fragmentary bottom perspective of the head end portion of a prone board of the present invention including a face supporting appliance with parts broken away and parts in section.

The trunk supporting structure 4 includes a trunk support 22 which overlies the head end portion of the frame. The upper edge of the trunk support projects beyond the frame end and the head end support and, preferably, has a lip 23 projecting rearwardly from such upper edge to shield a child from engagement with the hard frame and supporting structure and to prevent access by the patient to the assembly and adjusting fasteners beneath the trunk support. The trunk support 22 is shown partially in section in FIG. 11 illustrating typical construction of the padded patient contacting members. A rigid base plate B is covered on its surfaces which the patient is likely to contact by resilient padding material R, and upholstery material U covers the padding and is secured to the base plate. Before padding and upholstery materials are applied, suitable fasteners are secured to the base plate for use in subsequently assembling the padded members.

The trunk support 22 (hereinafter usually referred to as a chest support) is provided with bolts 24 which are inserted through bores 24′ in the web 14 of frame end support 2 and secured by wing nuts 24″. The chest support carries lateral support pads 25 for preventing or limiting lateral movement of the child's torso. Because the angle of inclination of the prone board usually will be below 90 degrees, the child normally will be maintained by gravity on the chest support. However, it may be desirable to provide restraint of movement away from the trunk support by inwardly inclining the lateral support pads 25 in the manner illustrated in FIG. 3. It is desirable to provide a hip strap 26 (FIG. 6) which may be fastened to one of the ventral supports such as the chest support 22 or an intermediate pad 27 (FIG. 10) or to a frame member 7 or 8.

The lateral support pads 25 are mounted by angle brackets 28 to chest support 22. Such pads 25 may be mounted in fixed position, as shown in FIG. 1, or may be adjustable either laterally or longitudinally relative to the trunk support 22, as shown in FIG. 8. For lateral adjustment, a plurality of bores 29 are provided to be attached by bolt and wing nut fasteners to the back of the chest support. The bolts may be studs like those shown at 24 or may be through bolts 30′. A rectangular offset in bracket 28 can embrace the lateral edge margin of chest support 22 to permit placement of pads 25 further inward beyond such lateral edge margin. A bolt 30′ extends through slot 30 extending longitudinally of the chest support 22. Bolt 30′ and wing nut 30″ clamp bracket 28 to chest support 22 in the desired position by selection of an appropriate bore 29 and by positioning bolt 30′ along slot 30. Therefore, the lateral pad position is adjustable according to the size of the child and to permit freedom of arm movement when a child is positioned with head and shoulders forward of the chest support upper edge, as shown in FIG. 5, such as for eating or playing. Other purposes for longitudinal adjustment of lateral pads will be described below.

Figure 9:
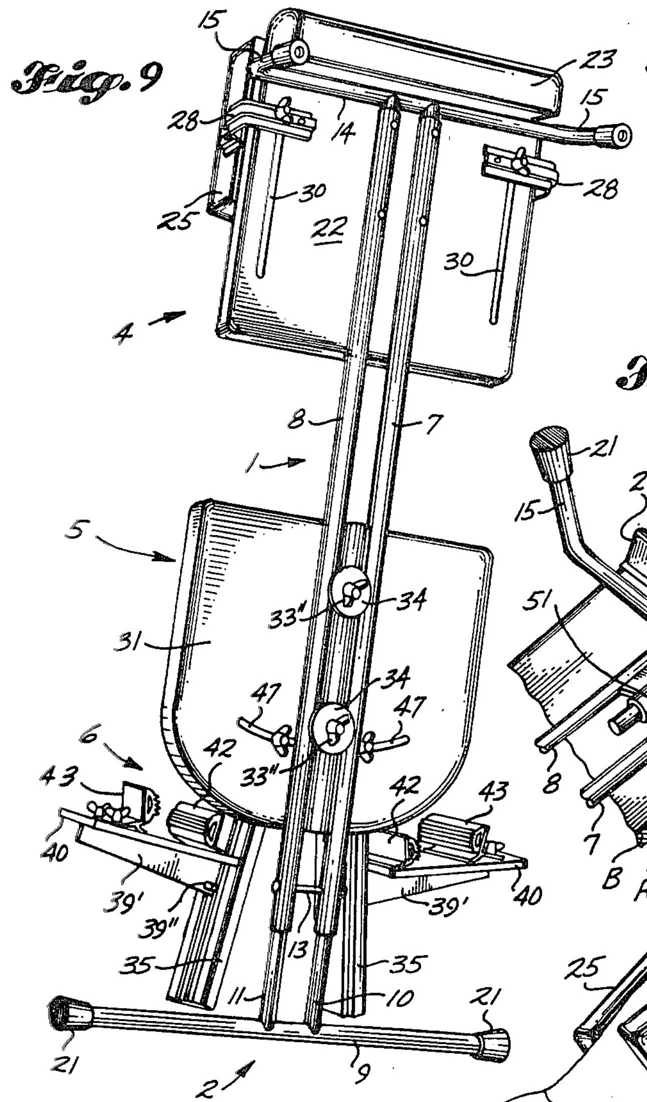
FIG. 9 is a bottom perspective of a prone board according to the present invention.

The knee and leg supporting structure 5 includes a leg support 31 which carries mounting tube 32 snugly receivable between the parallel spaced frame members 7 and 8, as shown in FIG. 9. The leg support pad 31 can be adjusted lengthwise of the frame in a position relative to trunk support 22 to fit a particular child. The pad should be positioned to support the knees and underlie adjacent portions of both the thigh and the lower leg. Leg support 31 is secured in the selected position by bolts 33 projecting through bores 33′ in mounting tube 32 to receive washer 34. Such washer preferably has an outside diameter approximately equal to or greater than the sum of the diameter of mounting tube 32 and the radii of frame tubes 7 and 8. The diameter of mounting tube 32 should be slightly less than that of frame tubes 7 and 8 to assure that washer 34 firmly engages the frame tubes. Wing nut 33″ is tightened to cinch washer 34 into firm engagement with tubes 7 and 8. Other fastening arrangements could be utilized to provide more positive connection with tubes 7 and 8, such as a bolt extending diametrally through tubes 7, 32 and 8, or a strap in place of washer 32 contoured to embrace tubes 7 and 8, with or without auxilary set screws.

Figure 7:
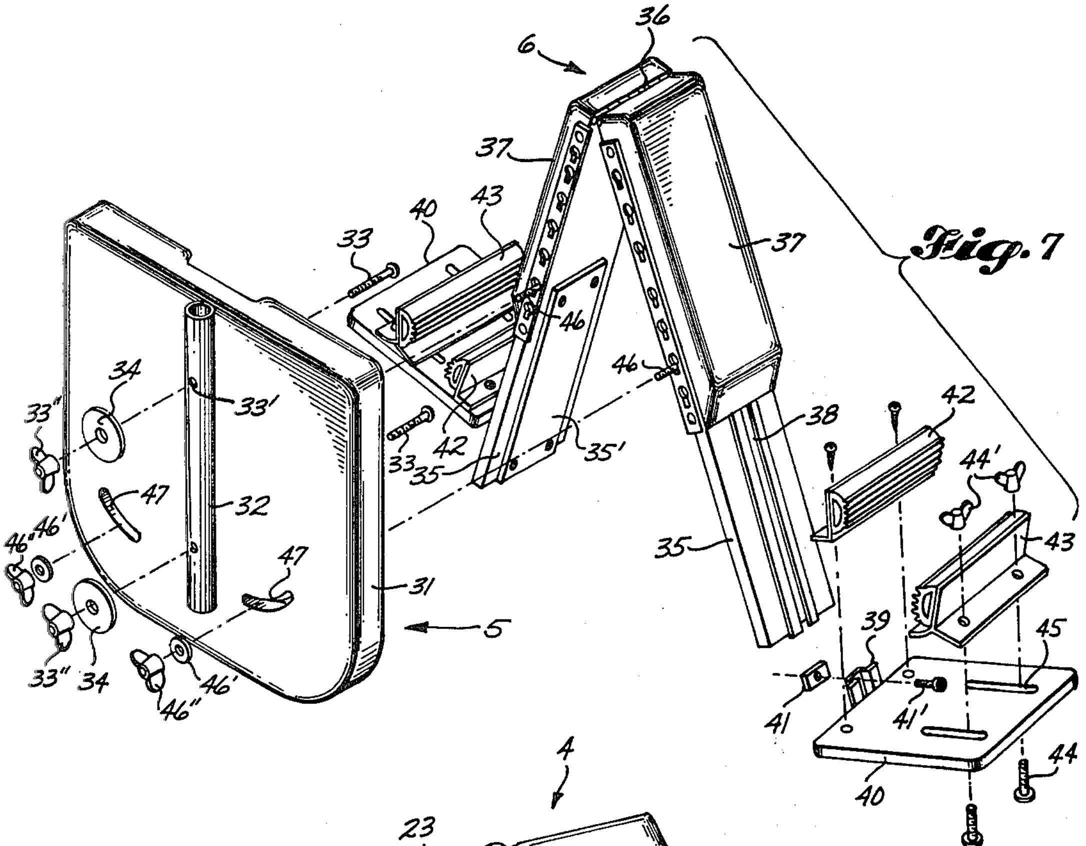
FIG. 7 is an exploded perspective of the knee, leg and foot supporting portions of a prone board according to the present invention.

The medial lateral leg and foot supporting structure 6 includes a pair of elongated leaves 35, the upper ends of which are connected together by a hinge 36. On the outer side of each leaf is a pad 37 which extends from the hinged leaf end a distance sufficient to insure engagement with the inner side of the patient's leg from a location between the crotch and the knee to a location below the knee, preferably to the fullest part of the lower leg. Leaves 35 and pads 37 constitute an interleg spacer against which the inner side of the patient's legs may abut when the feet are clamped as described hereinbelow. Such abutment of the legs against the spacer prevents misalignment of the leg bones by inward buckling of the bones. Such misalignment is prevented without clamping restraint on the legs. The portion of leaf 35 extending below pad 37 carries a longitudinal guide track 38 for receiving and guiding slide 39 of a foot supporting plate 40. The track may be recessed in leaf 35 and a reinforcing plate 35′ provided behind the track. The guide track shown in FIG. 7 is of outwardly opening channel shape with rectangularly return bent flanges by which a lock nut 41 is slidably retained. When the appropriate position of the foot plate 40 has been selected, bolt 41′ extending through slide 39 and into lock nut 41 is tightened to secure the slide in such selected position. A stiffening rib 39′ (FIG. 1) may be provided beneath plate 40 and may carry ears 39″ which bear on track 38 to prevent downward tilting of the outer edge of plate 40.

The foot plate projects transversely outwardly from leaf 35 for supporting the sole of the child's shoe. Lateral shoe clamping means restrains lateral movement of the child's respective leg. The clamping means carried on plate 40 includes an inner jaw 42 which is mounted in a fixed position at a location substantially aligned with pad 37 to limit the inward foot position and to prevent lateral bending of the ankle. Outer jaw 43 is mounted on the foot plate by bolts 44 and wing nuts 44′. The bolts project through parallel slots 45 in foot plate 40 which slots extend transversely of inner jaw 42 so that outer jaw 43 can be moved to clamp or release a shoe disposed between the clamp jaws. If it is desired to be able to dispose the clamp so that the shoe can be rotated to aid treatment of hip rotation, slide 39 can be carried by stiffener 39′ (FIGS. 1 and 6); and foot plate 40 can be mounted for movement relative to such stiffener by known swivel and clamping mechanism. Similarly, plate 40 could be adjustable relative to stiffener 39 for lateral movement of plate 40 to alter the position of inner jaw 42 relative to leaf 35.

The medial lateral leg and foot supporting structure 6 is mounted on leg support 31 by stud bolts 46 projecting forwardly from the edges of leaves 35, which bolts extend through arcuate slots 47 in support 31 and are secured by washers 46′ and wing nuts 46″. The arcuate slots are concentric with the axis of hinge 36 to permit spreading of leaves 35 for treating hip flexion and bolt 46, washer 46′ and nut 46″ secure each leaf in its selected spread position.

As indicated in FIG. 5, the prone board provides support for the trunk, legs and feet in suitable therapeutic positions while leaving the shoulders, arms and head free for feeding, eating or playing. However, the head is unsupported so that the utility of the prone board is limited to children who have sufficient neck control to support the head; and the time such children could spend on the prone board is limited by fatigue of neck muscles. A face support 48 to overcome such limitations is shown in FIGS. 6, 10, and 11.

As shown best in FIG. 11, the face rest has an oval frame 49 supported on one end of a rod 50. Such rod extends through an aperture in chest support lip 23 and into a split collar 51 carried by frame members 7,8. Clamp 52 maintains rod 50 in sleeve 51 and secures it against axial movement.

Oval frame or ring 49 carries a plurality of face pads including a chin rest 60, a forehead rest 61, jaw supports 62 and temple supports 63. Each of these members except the chin rest is supported from an individual collar 65 encircling a segment of ring 49 so that the pads can be individually adjusted along the ring and can be swung inwardly or outwardly about the collar axis. Consequently, the pads can be positioned to provide customized gentle support for each child. A setscrew 65' clamps the face pad collar 65 in the selected position.

The distance between the chin and forehead rests 60 and 61 can be altered by providing an oval frame 49 which is split into upper and lower segments. In the specific embodiment shown, the upper segment carries extension sleeves 66, each of which sleeves includes a setscrew 66' near its free end. The ends of the lower segment of frame 49 are inserted into the open ends of sleeves 66 to a greater or lesser extent depending on the desired distance between supports 60 and 61, and such lower segment frame ends are secured in the extension sleeves by setscrews 66'.

A scoliosis treating appliance 67 is shown in FIG. 6 carried by chest support 22. Such appliance includes a pair of arcuate pads 68 adjacent to opposite sides of the chest support and adjustable laterally and longitudinally relative to such chest support. In use, pads 68 would be turned 90 degrees from the position shown in FIG. 6 so that the chords of the pad arcs would be perpendicular to chest support 22. Such arcuate pad shape and disposition assures that the pads embrace the patient's sides and that he will be held securely between them. Each pad 68 is carried on the end of a rod 69 which extends through a collar 70 carried on a leg **71*a* of an angle bracket extending alongside and spaced from the lateral edge of chest support 22. The end of rod 69 opposite pad 68 preferably carries a handgrip 72 to facilitate control while moving pad 68 into the desired lateral position and while tightening knurled nut 73 which locks rod 69 and sleeve 70 against relative movement. Leg 71*b* of the angle bracket extends from leg 71*a* laterally of chest support 22 to underlie the chest support and longitudinal slots 30 in its backing board. Bolt 74, the head of which is received between the chest support base plate B (FIG. 11), and resilient padding material R projects rearwardly through the base plate and through an aperture in angle bracket leg 71*b*. The bracket is secured to the chest support by bolt 74** and a washer and wing nut (not shown).

Bolt 74 extends through a longitudinal slot 30 in the chest support base plate near its lateral edge and is slidable along such slot when its wing nut is loosened to adjust bracket leg **71*b* and, therefore, scoliosis pad 68 lengthwise of chest support 22. To facilitate such adjustment, a rigid channel member may overlie slot 30 between the base plate and the padding material to prevent interference with movement of the bolt head by the padding material. Alternatively, a guide track, lock nut and bolt arrangement like the foot support slide members 38, 41, 41' shown in FIG. 7 could be provided on the underside of chest support 22. When a chest support is provided with a scoliosis treating appliance 67 including a pair of independently adjustable pads 68, it is preferred that the chest support 22 have a lengthwise extent to support the ventral portion of the trunk substantially along the entire length of the spine and that the lateral pads 25** be relatively short and mounted adjacent to the upper edge of the chest support.

In the prone board having a frame head end support 3 of the type shown in FIG. 8 or 11, the angle of inclination a is determined by the height H (FIG. 5) of platform P and the length L of the prone board frame which may be fixed by the length of frame members 7 and 8 or may be adjustable by providing telescoping members 10 and 11 between such frame members and foot end support 9. In either case, use of the prone board is limited to the availability and location of stable platforms of suitable height. Greater mobility within a therapeutic facility or in day-to-day activity of a patient's family is provided by a freestanding prone board. Such a prone board can be inclined and the angle of inclination can be varied by use of the alternative supporting appliance 3' shown in FIG. 10.

Supporting appliance 3' is self-supporting from the same floor or ground level as that supporting the frame foot end support 2 and also provides for adjustment of the angle of inclination of the prone board. A prone board of the type shown in FIGS. 6, 8 and 9 can be converted to the self-supporting type by removing frame support 3 and attaching by bolts 20 and nuts 20' a plate carrying a collar (not shown) which receives the web 75 of the U-shaped support having long legs 76. Alternatively, web 75 may be mounted on the back of chest support 22 by a U-shaped bracket 75' (FIG. 13) in which the web can turn about its axis. The length of such legs 76 is greater than the height H of the web 75 from a floor F when the prone board is disposed at the maximum angle of inclination a so that the angle b (FIG. 12) between the plane of frame member 7,8 and the plane of support 75, 76 is always an obtuse angle. Such angular relationship is important to provide stability of the prone board.

A crossbar 77 connecting legs 76 and preferably located below the midpoint of the leg length receives a collar 78 carrying one end of a telescoping brace 79. The other end of brace 79 is connected between frame members 7 and 8 near the frame foot end support 2 by a diametral pivot pin 80. Handle 81 tightens a setscrew securing the telescoping members **79*a* and 79*b* of brace 79 in a selected position of legs 76. As suggested above, one end of brace 79 in pivotable about pin 80 and collar 78 supporting its opposite end is swingable about crossbar 77. Web 75 connecting the upper ends of legs 76 is pivotably mounted relative to frame members 7, 8 so that, when handle 81 is turned to release its setscrew, legs 76 can be swung to adjust the angle of inclination. To position the legs alongside the frame members 7, 8 for storage or transportation of the prone board, legs 76 would be swung forward of the chest support head end a distance sufficient to separate brace members 79*a* and 79*b*. Member 79*a* can then be swung about pivot 80 alongside frame members 7, 8, brace member 79*b* can be swung about crossbar 77 toward the plane of legs 76, and web 75 can be turned in bracket 75' to dispose legs 76 in a position alongside frame members 7, 8**.

An upper crossbar 82 spanning legs 76 and arcuate brackets 83 support a tray 84 on which the child can play or from which he can eat or be fed.

The stem of a caster 85 can be inserted through an aperture in the leg end cap 21 of each leg 76. Such casters are of conventional detent connecting type and include conventional locking mechanism to prevent rotation of the caster wheels when desired. Such casters are useful in a treatment facility for moving a child between examination and treatment locations, for example. By grasping the sides of the leg support 31, the frame foot end support 2 can be lifted slightly off the floor and the prone board wheeled from place to place. It is, therefore, unnecessary to remove the child from the prone board, carry him to a different location, place him in a secure location and then retrieve the prone board or, alternatively, require two persons to transport the child on the prone board in the manner of a stretcher. However, it is preferred that such casters not be provided on, or that they be removed from, prone boards which are used away from, a therapeutic facility, such as in the home, where locking the casters is more likely to be overlooked or where siblings may be likely to try pushing the prone board around, for example.

When the prone board of FIGS. 1 through 9 is to be used, the leg support 31 is positioned relative to trunk support 22 to fit the child to be supported thereon, and any desired intermediate pads 27 (FIG. 10) are attached in the same manner as leg support structure 5. The medial lateral leg supporting leaves 35 will be secured with the desired degree of spread between the free ends. The lateral pads 25 will be adjusted at least to be spaced apart sufficiently for the child to be received between them. The prone board is then preferably placed with both end supports 2 and 3 on the same level surface. The child can be placed on the prone board, and his feet positioned on the foot supporting plate 40 and clamped between jaws 42 and 43 of the shoe clamp. Lateral pads 25 can be adjusted if necessary to provide desired support and freedom of arm and shoulder movement, and hip strap 26 is secured. THe head end of the prone board would then be raised and placed on a platform P of the desired height H. If it is necessary to adjust the length L of the prone bord frame by adjustment of rods 10, 11 relative to frame tubular members 7, 8, such adjustment should be made prior to placing the child on the prone board. By placing the child on the prone board while it rests on a flat surface, he can be laid prone on such surface and lifted directly from such surface the short distance to the prone board. This is important especially for large or heavy children to reduce lifting. Also, in the flat position the child is unlikely to slip in any direction while being secured in the prone board.

In a clinic or other therapeutic facility, one prone board can be used for a number of different children at different times and suffering from various combinations and degrees of muscular or skeletal disorders because of the ease of making the adjustments and of interchanging or adding appliances.

More importantly, a prone board can be adapted to a particular child at a clinic from a few basic components and appliances, whereas prior standard prone boards have had limited utility in the range of disorders for which a prone board was useful; and usually prone boards have been custom-built heretofore to the specific needs of a particular child, adding to the already high costs of caring for a child suffering from muscular or skeletal disorders. Furthermore, prone boards of the present invention provide for adaptability to a wide range of changes in a child through the course of treatment and through growth.

Attachment of the head supporting appliance 48 permits use of the prone board during longer periods of time by reducing the strain on the neck muscles and permits use by infants prior to full development of the neck muscles or by children who have dysfunctional neck control. Not only does the head supporting appliance permit longer periods of therapeutic effectiveness of the knee and hip treating apparatus for which it is primarily used, but it affords the child greater participation in normal feeding, eating, playing and learning situations because he need not be confined to a bed for long periods, as was previously the case, nor does he require being held by another person in order to eat or play.

The medial lateral leg supporting structure 6 provides apparatus for more positively controlling treatment of hip rotation, abduction and extension and/or flexion by providing medial lateral support for the leg in addition to the ventral or dorsal support and foot control. It further provides means for aiding treatment of knee flexion which could not be accommodated by prior prone boards. Consequently, the child can be elevated to a more nearly upright position and the legs can support a greater proportion of the child's weight, thereby encouraging development of muscular strength and tone. This is so because the forces which tend to buckle the legs are counteracted by the interleg spacers 37. At the same time, the legs are free of clamping restraints which may cause discomfort and even injury.

Children who have scoliosis in addition to hip or knee disorders can be treated on the prone board. Furthermore, some treatment of scoliosis can be made more tolerable and less restrictive even if the prone board were not needed for hip or knee disorders, by permitting concurrent participation in other activity. If a child has lateral curvature of the spine at only one location, the pads of the scoliosis appliance 67 would be positioned along slots 30 at opposite sides of the trunk aligned substantially with the radius of spine curvature. The pads would then be moved inward to asymmetrical locations relative to the longitudinal plane of the prone board to the desired degree as determined by the therapist to urge the spine toward more nomal position. If a child's spine should have a reverse bend lateral curvature, a second scoliosis appliance could be provided or, in some instances, the pads of a single appliance may be offset longitudinally of the chest support 22 so that each pad is laterally aligned with the convex side of a lateral curve.

A prone board can be set by a therapist and with a few simple instructions to a child's guardian, the prone board can be used at home between treatments at a therapeutic facility. The therapist would set the appropriate degree of spread of medial lateral leg support leaves 35 and the location of the leg support 31 relative to chest support 22. The appropriate extension of telescoping members 7, 8 and 10, 11 could be set by a therapist; or a scale could be provided on a rod 10 or 11 to cooperate with the end of a corresponding tube 7 or 8, and the scale reading would be prescribed so that the prone board length could be reduced for transport and lengthened at home. The maximum height of a platform for supporting the frame head end support 3 or 3" also would be prescribed by the therapist and advice given such as the length of time that the prone board should be elevated or that the child could be supported in the prone board without undue fatigue.

If a face rest 48 is used, it is preferred that the therapist position pads 61, 62 and 63 to provide comfortable support without causing undesirable pressure on any part of the face. Also, the position of chin pad 60 relative to the foot clamping structure 40, 42, 43 would be set to avoid stretching the neck. The plane of ring 49 would normally be parallel to chest support 22. However, by turning rod 50 about its axis before tightening clamp 52, the plane of the ring can be tilted to provide comfort for a child whose head is biased toward one side. In most instances, it is preferred that the scoliosis appliance be utilized only under direct supervision of a therapist so that this appliance would normally be removed for home use.

Figure 12:
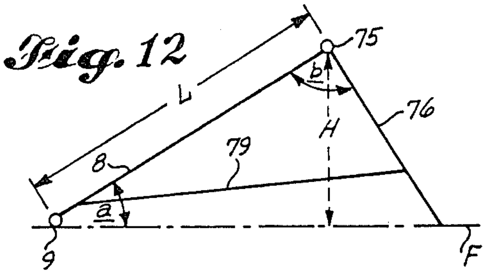
FIG. 12 is a diagrammatic side elevation of the prone board shown in FIG. 10 illustrating geometric relationships between components thereof.

When a self-supporting appliance 3' shown in FIGS. 10 and 12 is utilized, the angle of inclination a should be set before the child is placed on the prone board because the appliance is unstable during adjustment of legs 76 and telescoping brace 79. This appliance is especially useful when relatively large angles of inclination are desired or where platforms of suitable height are unavailable. While it is less convenient to measure the height H of web 75 than to measure that of a fixed platform, the angle of inclination could be set easily by providing a scale on the rod **79*a* of telescoping brace 79 to cooperate with the end of the tube 79*b*** receiving such rod.

I claim:

1. In therapeutic apparatus for use in treatment of muscular and skeletal disorders including an elongated frame having a foot end portion and head end portion, frame-supporting means for supporting the frame on a substantially level surface with the frame inclined upwardly toward the frame head end portion at an angle of inclination to such substantially level surface and body-supporting means carried by the frame and having a head end portion, for supporting a body in downwardly-facing position with the head beyond the head end portion of the body-supporting means, the improvement comprising the frame-supporting means including a freestanding supporting member projecting outwardly from the frame side opposite the body-supporting means and inclined away from the frame foot end portion, one end portion of said supporting member being pivotally mounted to the frame head end portion, means for maintaining the frame and said supporting member selectively in different angular relationships to each other including telescoping brace means adjustable in effective length and having one end portion connected to said supporting member at a location spaced from its pivoted end and its opposite end portion connected to the frame foot end portion for maintaining the frame in different angles of inclination to such substantially level surface corresponding to the adjusted length of said telescoping brace means, and a tray carried by the supporting member and projecting therefrom in a direction lengthwise of the frame away from the foot end portion thereof, said tray having a portion projecting beyond the head end portion of the body-supporting means.

2. In therapeutic apparatus for use in treatment of muscular and skeletal disorders including an elongated frame having a foot end portion and a head end portion, frame-supporting means for supporting the frame on a substantially level surface with the frame inclined upwardly toward the frame head end portion at an angle of inclination to such substantially level surface and body-supporting means carried by the frame and having a head end portion and a principal generally planar body front-engageable surface for supporting a body in downwardly-facing position with the head beyond the head end portion of the body-supporting means, the improvement comprising the frame-supporting means including a freestanding supporting member projecting outwardly from the side of the frame head end portion opposite the body-supporting means and inclined away from the frame foot end portion, one end portion of said supporting member being pivotally mounted to the frame head end portion, means for maintaining the frame and said supporting member selectively in different angular relationships to each other including telescoping brace means adjustable in effective length having one end portion connected to said supporting member at a location spaced from its pivoted end and its opposite end portion connected to the frame foot end portion for maintaining the frame in different angles of inclination corresponding to the adjusted length of said telescoping brace means, and head-supporting means carried by the frame and including a face-encircling ring located beyond the head end portion of the body-supporting means and disposed substantially in a plane generally horizontal and generally parallel to the body front-engageable surface of the body-supporting means, a plurality of discrete pads carried by said ring and located for engagement with opposite cheek portions of a downwardly-facing face and independent mounting means mounting said cheek-engageable pads on opposite sides of said ring, respectively.

* * * * *